United States Patent
Yant et al.

[11] Patent Number: 5,945,391
[45] Date of Patent: Aug. 31, 1999

[54] VEHICLE AND METHOD FOR STORING OZONE

[75] Inventors: Robert E. Yant, Medina; Marilyn M. Hurst; David B. Galluch, both of Hudson, all of Ohio

[73] Assignee: Quantum Technologies, Inc., Twinsburg, Ohio

[21] Appl. No.: 08/954,766

[22] Filed: Oct. 20, 1997

Related U.S. Application Data

[62] Division of application No. 08/744,853, Nov. 18, 1996, Pat. No. 5,705,468.

[51] Int. Cl.$^6$ .................................................. C01B 13/00
[52] U.S. Cl. ...................... 510/370; 510/372; 252/186.21
[58] Field of Search ..................... 510/370, 372; 252/186.21

[56] References Cited

U.S. PATENT DOCUMENTS

| | | | |
|---|---|---|---|
| 3,352,642 | 11/1967 | Heidt et al. | 23/222 |
| 3,406,117 | 10/1968 | Cook | 252/186 |
| 3,895,040 | 7/1975 | Miyazakis et al. | 260/413 |
| 4,045,347 | 8/1977 | Armstrong | 210/199 |
| 4,353,717 | 10/1982 | Herbrechtsmeier | 55/68 |
| 4,462,965 | 7/1984 | Azuma et al. | 204/176 |
| 4,572,821 | 2/1986 | Brodard et al. | 422/186.12 |
| 4,808,396 | 2/1989 | Shibanai et al. | 423/579 |
| 4,849,114 | 7/1989 | Zeff et al. | 210/747 |
| 4,861,497 | 8/1989 | Welch et al. | 210/759 |
| 4,970,005 | 11/1990 | Schuchart | 210/759 |
| 5,100,521 | 3/1992 | Schwarzl | 204/176 |
| 5,143,710 | 9/1992 | Sawyer et al. | 423/581 |
| 5,180,518 | 1/1993 | Sugihara et al. | 252/184 |
| 5,190,595 | 3/1993 | Ameen et al. | 252/143 |
| 5,366,703 | 11/1994 | Liechti et al. | 204/176 |
| 5,503,708 | 4/1996 | Koizumi et al. | 156/643.1 |
| 5,755,977 | 5/1998 | Gurol et al. | 210/759 |

OTHER PUBLICATIONS

JP223073; Jun. 9, 1988; Hitachi Plant Eng Const. "Cooling in Ozone Generating Device".
JP 401171621 A; Jul. 6, 1989 Decomposition of Ozone; Matsumura (See 1$^{st}$ Page).

*Primary Examiner*—Kishor Mayekar
*Attorney, Agent, or Firm*—Michael A. Centanni; Mark Kusner

[57] ABSTRACT

A vehicle and method for storing ozone is disclosed. A vehicle made of a water miscible, organic compound of a glycol-containing chemical compound, a tertiary alcohol or a mixture thereof that is capable of receiving and containing ozone gas is disclosed. The method involves producing ozone gas, introducing the ozone-containing gas into a mixing vessel that contains the aforementioned organic compound, agitating the organic compound in the presence of the ozone-containing gas, wherein the ozone-containing gas is at atmospheric pressure or at a pressure of up to about 150 psig., and releasing the pressure if pressures in excess of atmospheric are used.

8 Claims, 1 Drawing Sheet

VEHICLE AND METHOD FOR STORING OZONE

This is a divisional of application Ser. No. 08/744,853 filed on Nov. 18, 1996, now U.S. Pat. No. 5,705,468.

FIELD OF THE INVENTION

The present invention relates generally to ozone solutions, and more particularly to a vehicle and a method for storing ozone in high concentrations in solutions for extended periods of time.

BACKGROUND OF THE INVENTION

Ozone finds advantageous uses in numerous commercial applications. For example, ozone is a potent oxidizer, and as such, ozone is an effective disinfectant. Ozone may also be used to effectively control and eliminate various odors and colors in cleaning applications. Ozone has further applicability in the control of algae to improve biological stability in the water distribution system, in the destruction of natural and synthetic organic chemicals in industrial applications and is effective in the removal of iron and manganese from chemical systems.

A problem with ozone, however, is that it is an unstable gas. Ozone has a half-life of about twenty (20) to about thirty (30) minutes in distilled water at about 20 degrees Celsius. Ozone is even less stable in air.

Ozone's short half-life, both in air and in water, severely limits its commercial use. For this reason, ozone gas is not sold or shipped commercially.

The present invention overcomes this problem and provides a method and a vehicle for storing high, active concentrations of ozone for extended periods of time.

SUMMARY OF THE INVENTION

In accordance with an aspect of the present invention, there is provided a solution capable of receiving and releasing ozone gas, comprising a water miscible, organic compound selected from the group consisting of a glycol-containing chemical compound, a tertiary alcohol and a mixture thereof.

In accordance with another aspect of the present invention, there is provided a process for placing ozone gas into an organic solution, comprising the steps of producing ozone gas, introducing the ozone gas into a mixing vessel—the vessel containing a water miscible, organic compound selected from the group consisting of a glycol-containing chemical compound, a tertiary alcohol and a mixture thereof—and agitating the organic compound in the presence of the ozone gas until saturation or until a desired amount of ozone has been absorbed by the water miscible, organic compound.

In accordance with a further aspect of the present invention, there is provided a process for placing ozone gas into an organic solution, comprising the steps of producing ozone gas, introducing the ozone gas into a compressor, pressurizing the ozone gas, introducing the pressurized ozone gas into a vessel until an equilibrium pressure is achieved in the vessel—the vessel containing a water miscible, organic compound selected from the group consisting of a glycol-containing chemical compound, a tertiary alcohol and a mixture thereof—agitating the organic compound in the presence of the ozone gas, opening the vessel to bring the equilibrium pressure to atmospheric pressure and removing the ozonated organic compound from the vessel.

In accordance with another aspect of the present invention, the glycol-containing chemical compound may be polyethylene glycol, ethylene glycol, diethylene glycol, triethylene glycol, tetraethylene glycol, glycol ethers, polypropylene glycol, tertiary alcohols or combinations thereof.

In accordance with another aspect of the present invention, the above referenced glycols could be used individually or collectively in combination with other chemicals such as acetic acid, t-butanol or combinations thereof to increase the stability of ozone in solution; or, the above referenced glycols could be used individually or collectively with other chemicals such as hydrogen peroxide to enhance the beneficial properties of ozone.

It is an object of the present invention to provide a vehicle and a method for storing ozone at high, active concentrations for extended periods of time.

It is another object of the present invention to provide an ozonated, organic solution wherein the ozone remains stable and in solution for extended periods of time.

It is another object of the present invention to provide an ozonated, organic solution as described above which is soluble in water.

It is another object of the present invention to provide an ozonated, organic solution as described above wherein the organic solution includes a glycol-containing chemical compound.

It is another object of the present invention to provide an ozonated, aqueous solution capable of disinfection.

It is another object of the present invention to provide an ozonated, aqueous solution having a secondary disinfection agent, such as hydrogen peroxide, added thereto.

It is another object of the present invention to provide an ozonated, aqueous solution that is effective in removing colored spots and undesirable odors from fabric.

These and other objects of the present invention will become apparent to those skilled in the art upon a reading and understanding of the specification together with the attached drawings.

BRIEF DESCRIPTION OF THE DRAWING

The invention may take physical form in certain devices and arrangement of devices, a preferred embodiment of which will be described in detail in the specification and illustrated in the accompanying drawing which forms a part hereof and wherein.

DETAILED DESCRIPTION OF A PREFERRED EMBODIMENT

Figure 1:
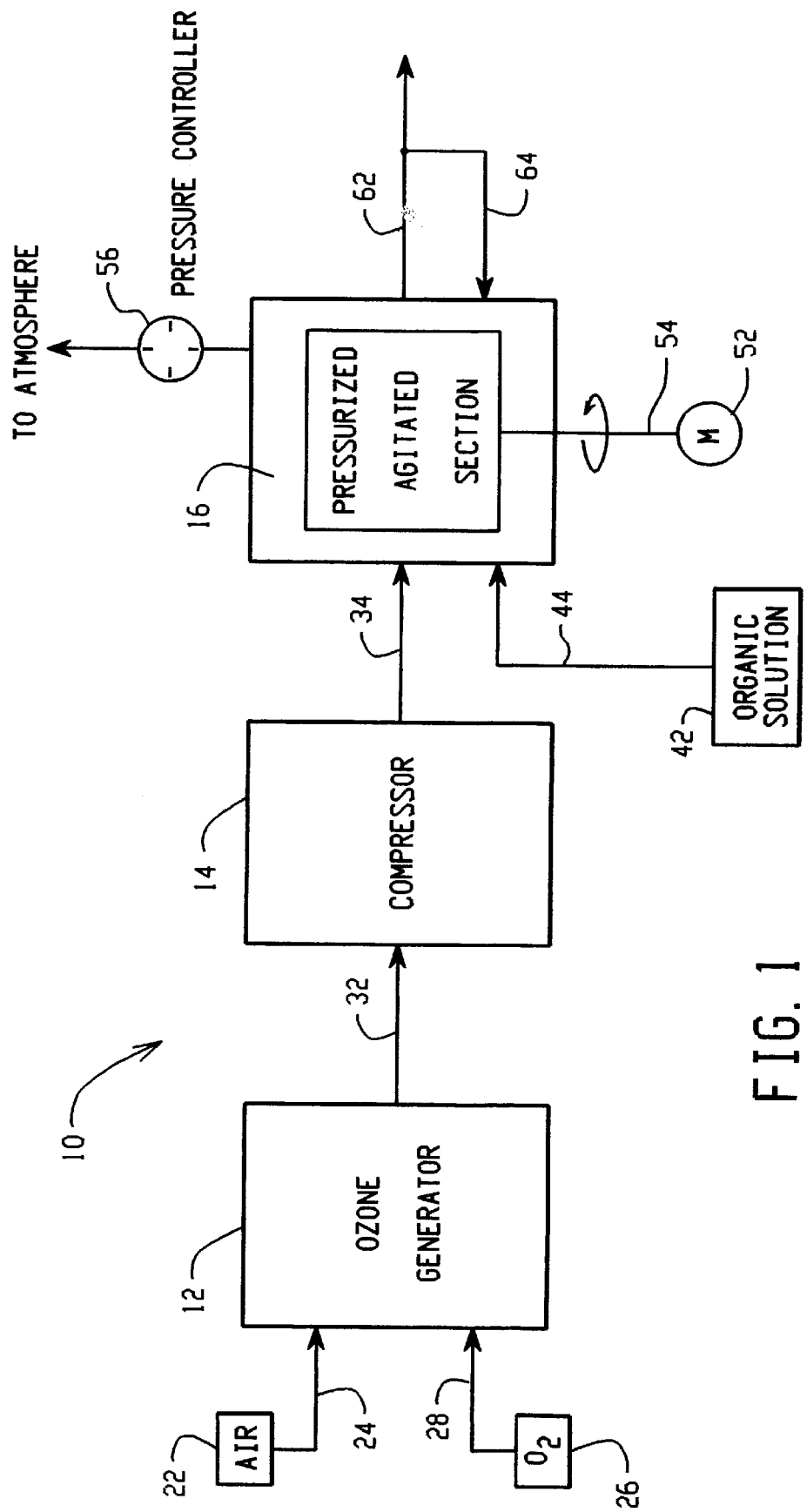
FIG. 1 is a schematic representation of a system placing ozone in an organic solution illustrating a preferred embodiment of the present invention.

Referring now to the drawing wherein the purpose is for illustrating a preferred embodiment of the invention only and not for the purpose of limiting the same, FIG. 1 shows a system 10 and a process for placing a high concentration of ozone in a stable, organic solution. Broadly stated, system 10 includes an ozone generator 12, a compressor 14 and a mixing device 16.

Ozone generator 12 is provided to generate ozone gas. Ozone gas is typically generated by exposing oxygen or an oxygen-containing gas to an electric arc. To this end, in the embodiment shown, an air source, designated 22 in FIG. 1, is connected to ozone generator 12 by line 24. An oxygen source, designated 26, is connected to ozone generator 12 by line 28. Air source 22 and oxygen source 26 may be used separately or in combination to provide an oxygen-containing gas to ozone generator 12.

A conduit 32 connects ozone generator 12 with compressor 14. Compressor 14 is connected to mixing device 16 by a conduit 34. Mixing device 16 is generally provided to mix the pressurized ozone with an organic solution. In FIG. 1, a source of organic solution 42 is schematically illustrated as being connected with mixing device 16 by conduit 44.

Mixing device 16 includes an interior mixing chamber (not shown) for blending the ozone gas with the organic solution. A mixing element (not shown) within the mixing chamber is driven by a motor 52 via shaft 54. According to the present invention, mixing device 16 is a pressurizable device. A pressure relief device 56, such as a conventional pressure relief valve, is preferably provided on mixing device 16, to vent excessive pressure within the mixing chamber to atmosphere. A conduit 62 is schematically shown in FIG. 1 to remove ozone-containing solution from mixing device 16. Conduit 62 includes a branch conduit 64 for returning all or a portion of the ozone-containing solution to mixing device 16.

Referring now to the operation of system 10, broadly stated, the process of placing a stable concentration of ozone in an organic solution is accomplished through the following steps. Oxygen-containing gas or pure oxygen is conveyed through conduits 24, 28 respectively to ozone-generating device 12. Ozone is generated in ozonator 12, conveyed to compressor 16 through conduit 32. Ozone gas in compressor 14 is pressurized and conveyed from the compressor 14 through conduit 34 to mixing vessel 16. In mixing vessel 16, the ozone is mixed together with an organic solution until an equilibrium pressure, i.e., compared to the pressure of the ozone-containing gas in conduit 34, is attained within the mixing chamber of mixing device 16. The pressure on the ozone-containing organic solution is removed, bringing the pressure inside the mixing chamber to atmospheric pressure. The ozonated, organic solution is removed from mixing device 16 via conduit 62. All or a portion of the ozone-containing solution may be returned to mixing device 16 to repeat the process to increase the concentration of ozone therein.

Referring now more specifically to the process of forming an ozone-containing solution according to the present invention, the process is begun by furnishing ozonator 12 with oxygen-containing gas, such as air, from source 22 or oxygen from source 26, or both. Ozone gas is generated within ozone generator 12. As indicated above, most ozonators generate ozone gas by exposing the oxygen or oxygen-containing gas to an electric arc. The electric arc of such ozonators may produce ozone gas ranging in concentration from about 0.1 percent (0.1%) ozone gas by volume to about fifteen percent (15%) ozone gas by volume. It is preferred that ozone gas is produced in as high a concentration of ozone as possible. Once produced, the ozone-containing gas is conveyed to compressor 14 through conduit 32.

Compressor 14 is provided to pressurize the ozone-containing gas. Preferably, the gas exiting compressor 14 has a pressure of up to about 150 psig. Examples of a suitable compressor include a liquid ring or a water piston compressor.

An organic solution from source 42 is deposited into mixing device 16 through conduit 34. The pressurized ozone-containing gas from compressor 14 is then fed to mixing device 16 through conduit 34 and the organic solution is then slowly agitated in the presence of the ozone-containing gas. In another embodiment of the invention, the ozone-containing gas may be introduced simultaneously with the introduction and agitation of the organic solution. In another embodiment of the invention, the ozone-containing gas is bubbled through the organic solution while the solution is slowly agitated. According to the present invention, the organic solution is preferably selected from the group of glycol-containing chemicals, tertiary alcohols or a combination of both.

Although the chemistry of the ozone/vehicle reaction is not well understood, it is believed that the ozone forms either a stable complex with the glycol-containing chemicals, or the tertiary alcohols, or that it reacts with glycol-containing chemicals, or tertiary alcohols, to form a new oxidizing compound. For purposes of this disclosure, reference will be made to ozone-containing solutions, even though the ozone may be present in the solutions as chemical complexes; or the ozone may have reacted with the vehicle, or other chemicals therein to produce a new, oxidizing compound; or the ozone may be present in the vehicle in some other physically or chemically unknown fashion.

The process as described herein may be implemented in either a batch or a continuous mode. In a batch mode, pressurized ozone-containing gas is fed to mixing device 16 until the pressure in conduit 34 comes to equilibrium with the pressure of the ozone-containing gas within the mixing chamber in mixing device 16. Pressure control device 56 is closed and ozone generator 12 is turned off. An organic solution of a glycol-containing chemical, a tertiary alcohol or a combination thereof is agitated in the presence of the pressurized, ozone-containing gas within mixing device 16 for about one (1) to about thirty (30) minutes, preferably for about one (1) to about ten (10) minutes and more preferably for about one (1) to about five (5) minutes. The aforementioned batch process may be repeated until a saturated ozone-containing solution is obtained. Typically, repeating the process from two (2) to four (4) times will result in a saturated solution.

In a continuous process, the pressurized, ozone-containing gas is fed continuously through conduit 34 to mixing device 16. Preferably, the pressure of the ozone-containing gas in conduit 34 is higher than the pressure of the ozone-containing gas in the mixing chamber of device 16. The ozone-containing gas is slowly bled through the organic solution within mixing device 16, as described hereinabove, and released through pressure controller 56.

Although the process described herein may be performed at room temperature, reducing the temperature of the organic solution may result in an increased ozone solubility and a concomitant increase in ozone concentration in the organic solution. To increase the ozone solubility and concentration in the organic solution, an ozone-containing gas temperature of about twenty (20) degrees Celsius may be used; a preferred temperature of the organic solution, as given hereinabove, of about ten (10) degrees Celsius may be used; and a most preferred temperature of the organic solution of about five (5) degrees Celsius may be used.

Examples of glycol-containing chemical compounds that may be used in the present invention include polyethylene glycol, ethylene glycol, diethylene glycol, triethylene glycol, tetraethylene glycol, glycol ethers, polypropylene glycol, tertiary alcohols or combinations thereof.

Final ozone concentrations that may be obtained in polyethylene glycol using the process disclosed herein range up to about twelve (12) grams of ozone per liter of polyethylene glycol.

Table I illustrates final ozone concentrations that may be obtained in polyethylene glycol. Also indicated are pressures of ozone-containing gas within mixing device 16 and times of exposure of the polyethylene glycol vehicle to the ozone containing gas. For the data presented in Table I, the concentration of ozone in the feed stream, and therefore in the mixing vessel, is about six percent (6%).

TABLE I

SOLUTION OZONE

| TIME OF OZONE FLOW | MIXING VESSEL PRESSURE | CONCENTRATION IN POLYETHYLENE GLYCOL |
| --- | --- | --- |
| 120 minutes | 20 psig | 4,610 mg/l |
| 240 minutes | 20 psig | 6,140 mg/l |
| 480 minutes | 20 psig | 6,680 mg/l |
| 25 minutes | 94 psig | 11,710 mg/l |

After the indicated amounts of time, the pressure in mixing vessel 16 was reduced to atmospheric pressure.

Any of the organic solutions containing ozone described herein may be solubilized in water to a desired concentration of ozone.

The processes and chemistries disclosed herein produce stable concentrations of ozone in aqueous solutions making the storage of ozone-containing solutions in containers and the subsequent shipment thereof a practical reality. The data of Table II illustrate the stability of ozone that may be obtained in polyethylene glycol through the processes of the present invention.

TABLE II

| TIME SINCE PREPARATION (Days) | OZONE STRENGTH mg/l |
| --- | --- |
| 0 | 11,710 |
| 3 | 11,520 |
| 4 | 11,040 |
| 20 | 7,780 |
| 36 | 4,970 |

It may be seen from these data that even after thirty-six (36) days the concentration of ozone in polyethylene glycol is still very high at 4,970 mg/l.

The solubility of ozone in distilled water at twenty (20) degrees Celsius is about 8.92 mg/l. In contrast, the concentration of ozone in polyethylene glycol, even after thirty-six (36) days as made in accordance with the processes of the present invention, is 1,300 times as large.

The data of table II are to be contrasted with the instability of ozone in distilled water. An initial concentration of ozone in water of 1.30 grams per liter, at a water temperature of ten (10) degrees Celsius, drops to zero (0) grams per liter in just twenty (20) hours.

As previously mentioned, an organic vehicle of the present invention that has been charged with ozone may be further diluted in water. Table III illustrates the ability of such an aqueous system composed of polyethylene glycol charged with ozone to maintain its concentration of ozone for up to thirty-five (35) days without any measurable loss of ozone concentration. These data of Table III are to be contrasted with the aforementioned loss of ozone in water after just twenty (20) hours.

TABLE III

| TIME SINCE PREPARATION (Days) | OZONE STRENGTH (PPM) |
| --- | --- |
| 0 | 84 |
| 1 | 84 |
| 3 | 96 |
| 6 | 90 |
| 14 | 84 |
| 35 | 84 |

The organic vehicles of the present invention may be used as described herein, or they may be used in combination with other chemicals designed to enhance the stability of ozone in solution or in combination with chemicals designed to enhance the disinfection properties of ozone. Examples of chemicals that may be added to enhance the ozone stability in solution include acetic acid, t-butanol and combinations thereof. An example of a secondary disinfection agent that may be added to the organic vehicle described herein is hydrogen peroxide.

The present invention has been described with respect to preferred embodiments and a preferred method of forming the same. Other alterations and modifications will occur to others skilled in the art upon their reading and understanding of this specification. It is intended that all such modifications and alterations fall within the scope of the invention as claimed and the equivalents thereof.

Having described the invention, the following is claimed:

1. An ozone-containing fluid, comprising: an organic compound in liquid form selected from the group consisting of polyethylene glycol, diethylene glycol, triethylene glycol, polypropylene glycol, glycol ethers, a tertiary alcohol and mixtures thereof; and, a concentrated amount of ozone of at least 4.97 grams per liter dissolved in said organic compound as $O_3$ to form a stable ozone-containing fluid, said stable fluid capable of storing and maintaining the concentrated amount of ozone in the fluid for several days as compared to the fluid without any of said organic compound.

2. The ozone-containing fluid of claim 1, further comprising water.

3. The ozone-containing fluid of claim 1, wherein said concentration of ozone is up to about eleven and one-half grams per liter of said organic compound.

4. The ozone-containing fluid of claim 2, further comprising acetic acid, t-butanol or combinations thereof.

5. The ozone-containing fluid of claim 4, further comprising hydrogen peroxide.

6. The ozone-containing fluid of claim 2, further comprising hydrogen peroxide.

7. A disinfectant for use in treating infections, comprising:

(A) an organic compound in liquid form selected from the group consisting of polyethylene glycol, diethylene glycol, triethylene glycol, polypropylene glycol, glycol ethers, a tertiary alcohol and mixtures thereof;

(B) a chemical mixed with said organic compound to form a stable solution, said chemical selected from the group consisting of acetic acid, t-butanol, hydrogen peroxide and combinations thereof; and, (C) a concentrated amount of ozone of at least about 4.97 grams per liter dissolved in said stable solution to form a stable ozone-containing disinfectant, said stable solution capable of storing and maintaining the concentrated amount of ozone in the disinfectant for several days as compared to the disinfectant without any of said organic compound.

8. The disinfectant of claim 7, wherein said disinfectant further includes water.

* * * * *